United States Patent
Owen (10) Patent No.: US 9,849,283 B2
(45) Date of Patent: Dec. 26, 2017

(54) METHOD TO TREAT VASCULAR DYSFUNCTION THROUGH ENHANCED VASCULAR FLOW AND HEMODYNAMIC ACTIVATION OF THE AUTOCRINE AND PARACRINE PROCESSES

(71) Applicant: John M. Owen, Tulsa, OK (US)

(72) Inventor: John M. Owen, Tulsa, OK (US)

( * ) Notice: Subject to any disclaimer, the term of this patent is extended or adjusted under 35 U.S.C. 154(b) by 0 days.

(21) Appl. No.: 15/010,750

(22) Filed: Jan. 29, 2016

(65) Prior Publication Data

US 2017/0216591 A1 Aug. 3, 2017

(51) Int. Cl.
*A61N 1/36* (2006.01)
*A61N 1/04* (2006.01)

(52) U.S. Cl.
CPC ....... *A61N 1/36014* (2013.01); *A61N 1/0452* (2013.01); *A61N 1/0484* (2013.01); *A61N 1/0492* (2013.01); *A61N 1/36003* (2013.01)

(58) Field of Classification Search
CPC ............ A61N 1/36114; A61N 1/36117; A61N 1/36014
See application file for complete search history.

(56) References Cited

U.S. PATENT DOCUMENTS

| | | |
|---|---|---|
| 5,139,020 A | 8/1992 | Koestner et al. |
| 5,199,428 A | 4/1993 | Obel et al. |
| 5,556,422 A | 9/1996 | Powell, III et al. |
| 5,807,556 A | 9/1998 | Mannion et al. |
| 6,058,331 A | 5/2000 | King |
| 6,200,259 B1 | 3/2001 | March |
| 6,522,929 B2 | 2/2003 | Swing |
| 7,340,298 B1 | 3/2008 | Barbut |
| 9,403,000 B2 * | 8/2016 | Lyons .................. A61B 5/7275 |
| 2007/0027496 A1 * | 2/2007 | Parnis .................. A61N 1/3601 607/42 |
| 2008/0132969 A1 | 6/2008 | Bennett et al. |
| 2008/0195174 A1 | 8/2008 | Walker et al. |
| 2012/0053655 A1 * | 3/2012 | Bain ...................... A61N 1/205 607/48 |

OTHER PUBLICATIONS

International Search Report of the International Searching Authority mailed by ISA/USA, U.S. Patent and Trademark Office dated Feb. 23, 2017 for International Patent Application No. PCT/US2017/015651.

* cited by examiner

*Primary Examiner* — Michael D Abreu
(74) *Attorney, Agent, or Firm* — Law Office of Jeff Williams; J. Oliver Williams (57) ABSTRACT

A method and system for creating shear stress and endothelial mechanotransduction through neuromuscular stimulation of the muscle pump. Chronic application a minimum of 30 days triggers the autocrine and paracrine processes which elevates production of vasoactive substances including nitric oxide, prostacyclin, superoxide dismutase, thrombomodulin, glutathion, Krupple-like factor 2 and many others. Chronic application also promotes angiogenesis and development of collateral circulation. This is a cost-effective, non-invasive, drug-free therapy to treat vascular dysfunction and ameliorate or reverse its effects on cardiovascular health.

18 Claims, 7 Drawing Sheets

METHOD TO TREAT VASCULAR DYSFUNCTION THROUGH ENHANCED VASCULAR FLOW AND HEMODYNAMIC ACTIVATION OF THE AUTOCRINE AND PARACRINE PROCESSES

BACKGROUND

1. Field of the Invention

The present application relates to a method of medical treatment, and more particularly to a method for treating people with vascular health problems by the application of neuromuscular stimulation leading to the generation of endothelial mechanotransduction, which boosts endocrine, autocrine and paracrine activity resulting in an increase in vasoactive substances.

2. Description of Related Art

Blood vessels traverse all throughout our bodies. The endothelium is the inner lining of all blood vessels. It is the largest organ in the body. If flattened and spread out, it is equivalent in size to approximately six tennis courts. Once thought to be inert and unimportant, research has shown it to be an extremely important organ that exerts control over an array of mechanisms which serve to maintain vascular tone and blood fluidity by:

Maintaining vascular smooth muscle tone
Regulating angiogenesis and cell proliferation
Mediating inflammatory and immune responses
Regulating vascular permeability
Regulating thrombolysis
Regulating leukocyte adhesion
Regulating platelet adhesion and aggregation
Regulating lipid oxidation The endothelium exerts this control through endocrine, paracrine and autocrine processes wherein the endothelial cells secrete vasoactive substances such as hormones, genes, proteins, transcription factors and others, resulting in the regulatory actions listed above. This group of events is generally known as, "endothelial mechanotransduction." Mechanotransduction refers to the processes through which cells sense and respond to mechanical stimuli by converting them to biochemical signals that elicit specific cellular responses. While shear stress and mechanotransduction are well documented in the literature, no one has proposed the use of endothelial mechanotransduction as a therapy.

Endothelial mechanotransduction happens in response to blood flow and laminar shear stress, induced from the mechanical forces caused by the rubbing of blood cells on the endothelium (the lining of blood vessels). When people are young, the normal physiologic levels of blood flow and shear stress keep blood vessels (and the whole cardiovascular system) healthy. Later in life, people make diet and lifestyle choices that can lower blood flow, clog the blood vessels with fatty deposits and impair the regulatory processes necessary for vascular health. The endothelium can then become dysfunctional contributing to atherosclerosis (hardening of the arteries), diabetes, hypertension (high blood pressure), delayed wound healing, vasculitis, congestive heart failure, critical limb ischemia, neuropathy and more.

Endothelial dysfunction is a major health problem in the U.S. with more than 65,000 peer-reviewed articles on this topic. Various different methods have been used, experimentally, to treat endothelia dysfunction. Methods involve the use of drugs, or external compression devices.

There are drugs labeled "NO donors" which cause the body to generate NO and several are in current tests to determine their efficacy and safety. Aside from nitroglycerin, few have made it into the marketplace and the only one in widespread use is for erectile dysfunction. Erectile dysfunction, like endothelial dysfunction, is caused by a lack of NO. These drugs can have many disadvantages and undesirable side effects when used.

Although electrical stimulation for medical purposes has been in use for more than a hundred years, its use has largely been defined by the effects of various types of current (i.e., galvanic, interferential, "Russian", faradic, high voltage pulsed current, micro-current, etc.). In current practice, electrical stimulation is primarily used by physicians, physical therapists, chiropractors, athletic trainers and rehabilitation facilities for the following purposes: sore and torn muscles and tendons, bone fractures, healing of decubitus and diabetic ulcers, pain alleviation, relief from muscle spasms and treatment for disuse atrophy. The localized, minor movement of blood is often mentioned as part of the treatment. Functional electrical stimulation (FES) is primarily used to retrain muscles in patients with spinal cord or neuronal injury.

There are also electrical stimulators in use for narrowly defined special uses, including: implanted spinal stimulation for pain alleviation, implanted stimulation of the vagus nerve for epilepsy, U.S. Pat. No. 5,928,272, Adkins, et al (1999) and FES units for pharyngeal muscle re-education for the act of swallowing, U.S. Pat. No. 6,104,958, Freed et al (2000).

Several devices on the market produce electrical stimulation waveforms adequate to contract skeletal muscle (i.e. Rich-Mar Corp's Theratouch 4.7, Pro-Med's model 7560, Microvas Technologies' models I and II, NeuroCare's NC1000), all of these devices, however, apply stimulation to several treatment locations simultaneously, which can create back pressure thus reducing the pumping action of the one-way valves in the venous system. Furthermore, all of these devices have an inadequate number of leads to treat the large areas or to generate the volume and velocity needed to reach therapeutic levels of mechanotransduction.

Several devices have attempted to achieve upregulated blood flow through means of externally applied hydraulic pressure as shown in U.S. Pat. No. 6,863,670 to Zheng (2005), or pneumatic pressure as in U.S. Pat. No. 6,358,219 to Arkans (2002). In these applications, the invention squeezes the leg by way of inflatable cuffs around the leg. The veins, in the muscles, are also squeezed, although much of the pressure is absorbed by the relaxed muscle mass which acts as a cushion to dissipate the pressure. A problem common to external compression is chaffing and bruising from the extreme pressures and repetitive squeezing of the cuffs.

While these inventions do manage to accomplish some movement of blood, their method is limited in effectiveness because they are squeezing through thick layers of relaxed muscles, forming a cushion and the squeezing forces are therein blunted. It is desired that pressure be applied directly to the veins in a manner similar to that seen with typical body movements.

One novel form of stimulation for blood flow is U.S. Pat. No. 5,195,518 to Mannion, et al (1993) which involves the surgical attachment of skeletal muscles to the heart, then applying stimulation to the attached muscle in an attempt to drive blood to an ischemic heart. The extreme costs and invasive nature of this invention would tend to limit its application.

Although some small strides have been made to treat endothelial dysfunction, considerable shortcomings remain.

A therapy for the creation of endothelial mechanotransduction and thereby restores vascular homeostasis is needed.

SUMMARY OF THE INVENTION

The system and method of the present application is designed to reverse endothelial dysfunction through activation of the paracrine and autocrine processes in the endothelium. A method for creating endothelial mechanotransduction is disclosed. It provides a method for generating enhanced blood flow. By treating large areas of the body with multiple treatment pads, and by treating with sequential, overlapping intervals of contractions from distal to proximal, the method "milks" blood from the extremities, elevating blood flow and venous return.

This upregulated blood flow, by frictional drag on the endothelial wall, elevates laminar shear stress and increases mechanotransduction. Through mechanotransduction, the autocrine/paracrine functions of the endothelial cells increase the production of vasoactive substances including nitric oxide, prostacyclin, SOD and many others. Advantages of the invention include a cost-effective, non-invasive, drug-free treatment for a wide variety of vascular-related illnesses including atherosclerosis, hypertension, heart failure, vasculitis, neuropathy, chronic wounds and the effects of diabetes.

The method includes the use of a specific waveform generating device. Its specific electrical current and specific waveforms need only to be adequate to induce short periods of tetanic skeletal muscle contractions which will compress the venous system and, by way of the one-way valves in the veins, pump the blood toward the heart. This is generally known as the venous muscle pump. The treatment of endothelial dysfunction by physical movement of blood is a new and improved method.

An object of the present application is to provide the benefits of endogeneous (generated inside the body) NO and the restoration of endothelial function, without the disadvantages and potential side effects of drug use. Another object of the present application is to describe a system and method configured to provide a process and device having an adequate number of leads to treat the large areas of the body and to generate the volume and velocity needed to induce or increase therapeutic levels of endothelial mechanotransduction.

DESCRIPTION OF THE DRAWINGS

The novel features believed characteristic of the application are set forth in the appended claims. However, the application itself, as well as a preferred mode of use, and further objectives and advantages thereof, will best be understood by reference to the following detailed description when read in conjunction with the accompanying drawings, wherein:

While the system and method of the present application is susceptible to various modifications and alternative forms, specific embodiments thereof have been shown by way of example in the drawings and are herein described in detail. It should be understood, however, that the description herein of specific embodiments is not intended to limit the application to the particular embodiment disclosed, but on the contrary, the intention is to cover all modifications, equivalents, and alternatives falling within the spirit and scope of the process of the present application as defined by the appended claims.

DETAILED DESCRIPTION OF THE PREFERRED EMBODIMENT

Illustrative embodiments of the preferred embodiment are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in other desired orientations. Thus, the use of terms to describe a spatial relationship between various components or to describe the spatial orientation of aspects of such components should be understood to describe a relative relationship between the components or a spatial orientation of aspects of such components, respectively, as the device described herein may be oriented in any desired direction.

The system and method in accordance with the present application overcomes one or more of the above-discussed problems commonly associated with conventional methods for the treatment of endothelial dysfunction. It is designed to treat endothelial dysfunction through activation of the paracrine and autocrine processes in the endothelium by creating endothelial mechanotransduction. The process involves providing electrical stimulation to skeletal muscles over large areas of the body with multiple treatment pads that are sequentially initiated in overlapping intervals to elevate blood flow and venous return.

This increased blood flow creates increased frictional drag on the endothelial wall between blood cells and the endothelial wall itself. This laminar shear stress directly applied to the endothelial wall creates mechanotransduction. Through mechanotransduction, the autocrine/paracrine functions of the endothelial cells increase the production of vasoactive substances including nitric oxide, prostacyclin, SOD and many others. This process avoids invasive procedures and the risks associated with drugs. These and other unique features of the device are discussed below and illustrated in the accompanying drawings.

The system and method will be understood, both as to its structure and operation, from the accompanying drawings, taken in conjunction with the accompanying description. Several embodiments of the system may be presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless otherwise described.

The system and method of the present application is illustrated in the associated drawings. The assembly includes a controller, such as a waveform generating device. The controller induces an electrical current through a plurality of treatment pads coupled to a human body. The treatment pads are sequentially initiated by the controller in short overlapping periods. The electrical stimulation causes contractions which will directly compress the venous system. By way of the one-way valves in the veins, the sequential stimulation pumps the blood toward the heart.

Figure 1:
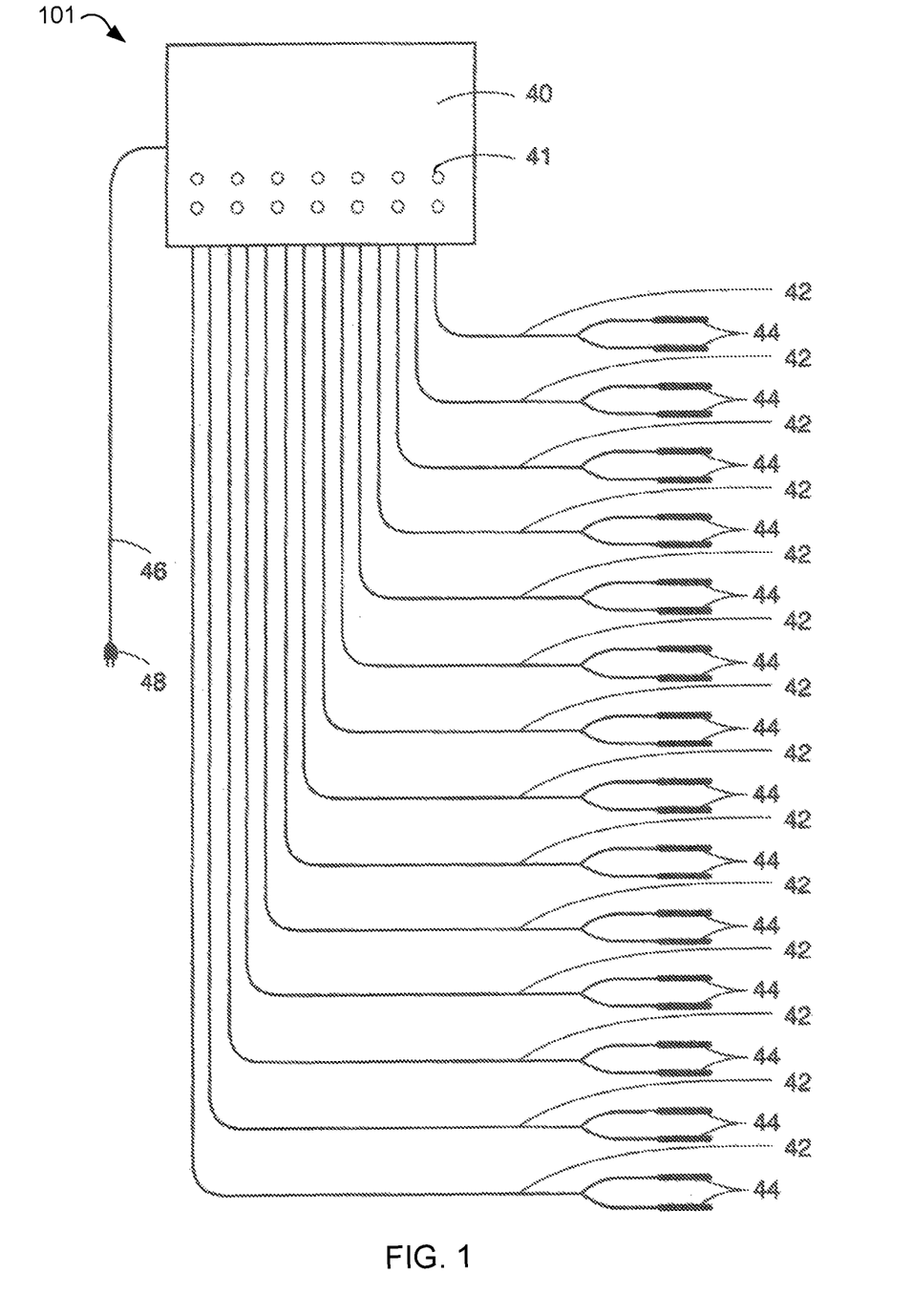
FIG. 1 is a view of the general configuration of the electrical stimulation system according to the preferred embodiment of the present application.

Referring now to the drawings wherein like reference characters identify corresponding or similar elements in form and function throughout the several views. FIG. 1 illustrates the general configuration of the electrical stimulation system 101. System 101 includes controller 40 having a plurality of leads 42 that are connected together via treatment pads 44. Treatment pads 44 are configured for attachment to the human body. A plurality of pads 44 are coupled along the same vein in a predetermined pattern. The pads 44/leads 42 are used to conduct the waveforms into and through the tissue being treated. Knobs 41 are also included and serve as a means of controlling the intensity of the waveform transferred through pads 44. An operator is able to regulate the waveform as needed.

Controller 40 is operated by electrical power provided through a power source. As seen in FIG. 1, a plug 48 and power cord 46 may be included. System 101 is configured to receive power from the power source and transmit an electrical stimulation signal through leads 42 to the skeletal muscles of the human body. Each vein is surrounded by muscles that, when stimulated, apply pressure directly to the veins in the same way the body normally does to move blood. System 101 is not limited to a particular power source or voltage. An example is an 18-volt power source.

Controller 40 is configured to process and regulate the timing and sequence of electrical stimulations. This may be done via a processing unit and a plurality of controlling devices, such as a timer, a rheostat, and a gating device for example. Controller 40 controls the duration, intensity, and sequence of the waveform. Controller 40 is configured to regulate the intervals of treatment at pads 44. The length of time may be limited to one half second, up to a plurality of seconds for example.

It is understood that system 101 may include any number of leads 42 and pads 44. Furthermore, pads 44 may be releasably coupled to the human body using methods common in the industry. Such methods may include, but are not limited to the use of adhesives, manual straps, hook and loop fasteners, elastic, and other garments. Each is configured to hold pads 44 in place during treatment. Additionally, although a wire lead has been described, the leads may use technology to permit wired and/or wireless methods of electrical transmission.

System 101 uses neuromuscular stimulation applied at multiple locations on any and all extremities of the human body to contract skeletal muscles in a sequential pattern, beginning from a distal location to a proximal location on the extremity. This increases the blood flow to the heart thereby instigating more frictional drag between blood cells and the endothelial layer. The shear stress produces increased mechanotransduction activating the paracrine and autocrine processes listed above.

Figure 2:
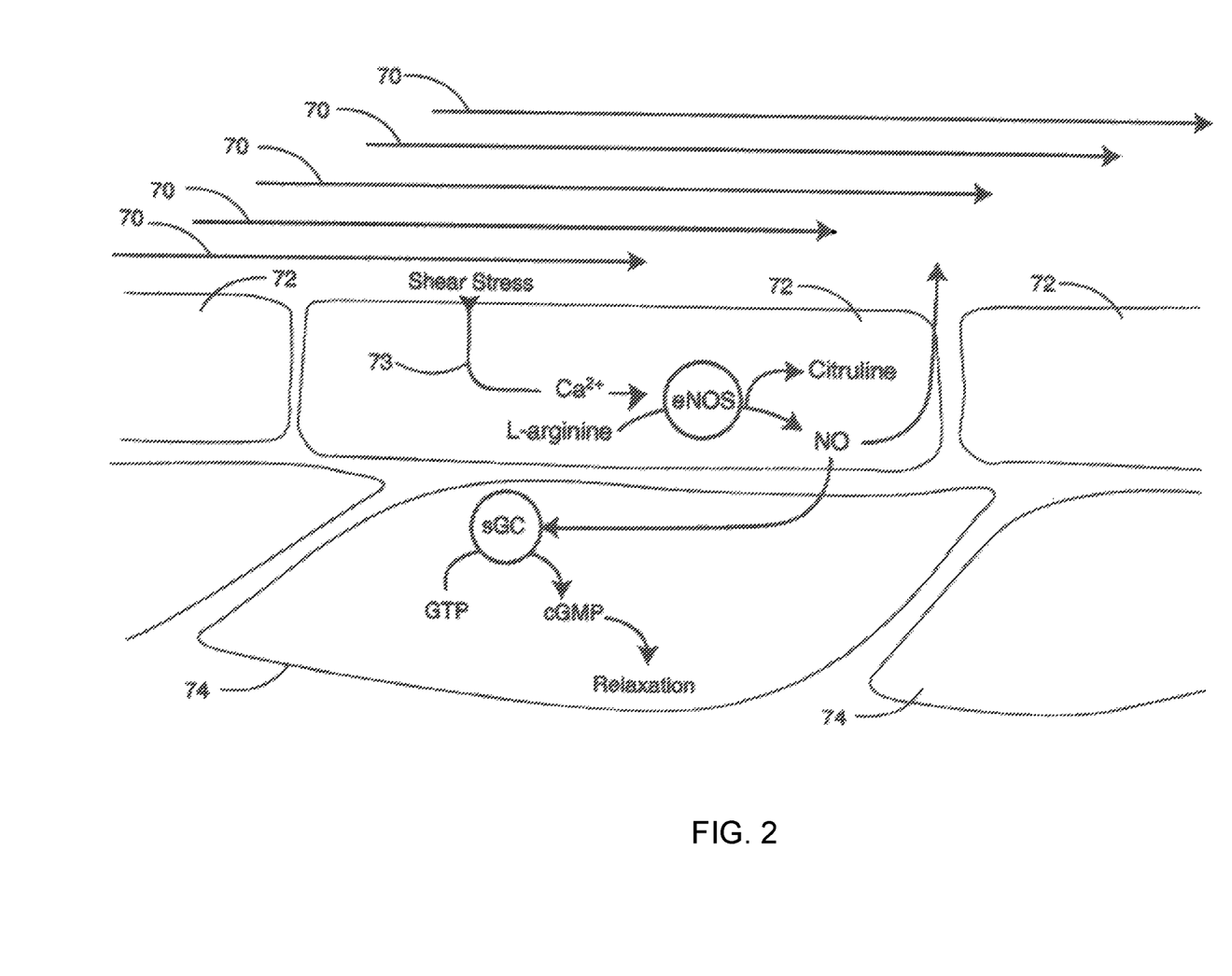
FIG. 2 is a view showing the cellular basis of mechanotransduction.

Referring now also to FIG. 2 in the drawings, a view showing the cellular basis of mechanotransduction is illustrated. As stated previously, the contraction of the skeletal muscles directly compresses the blood vessels in the body, causing increased blood flow in the blood vessels. Blood 70 flows through the blood vessels in a laminar fashion, meaning that blood in the center flows more rapidly than the blood adjacent to the endothelial cells 72 of the lining within the blood vessel. The flow is varied due to the frictional forces. These frictional forces create shear stress on the endothelial cells 72. Shear stress transduces the stresses into chemical signals 73. These chemical signals 73 travel through a calcium pathway to activate endothelial nitric oxide synthase (eNOS) which synthesizes citruline and nitric oxide (NO) from L arginine. Some of the NO immediately migrates into the smooth muscle cells 74 where it converts guanosine triphosphate into cyclic guanosine monophosphate. The cyclic guanosine monophosphate causes relaxation in the smooth muscle cells resulting in vasodilation. The balance of the NO, and other secretagogues, migrate into the veins and arteries.

Figure 3:
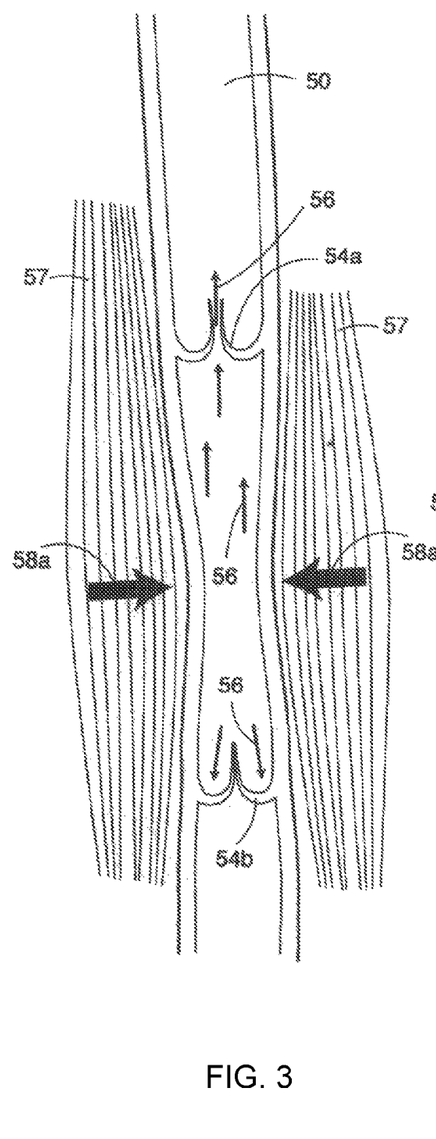
FIGS. 3 and 4 are a representative side view of the effects of the electrical stimulation system of FIG. 1 on blood vessels.
Figure 4:
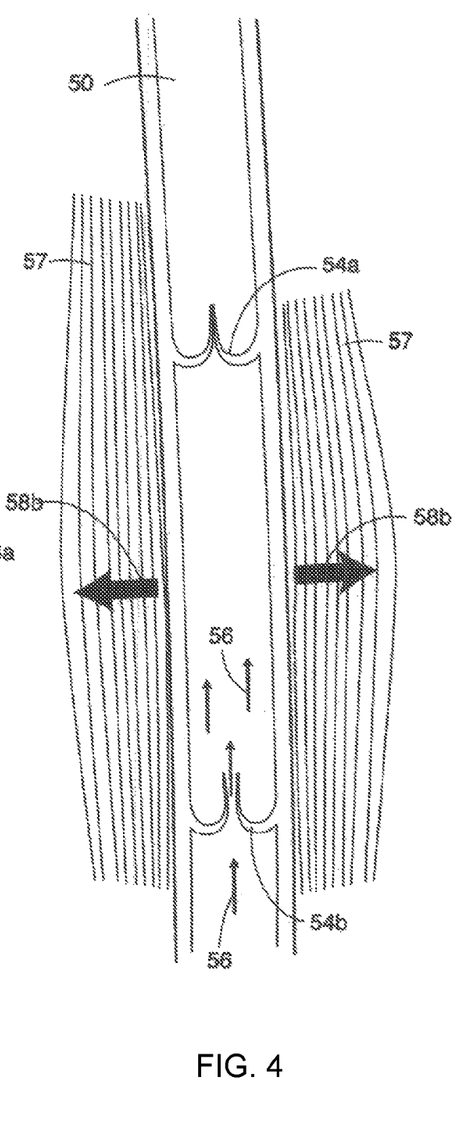

Referring now also to FIGS. 3 and 4 in the drawings, a representative side view of a blood vessel using system 101 is shown. As seen in FIG. 3, electrical stimulation causes the skeletal muscles 57 to contract (see arrows 58a) which compresses the vein 50. This compression forces the blood 56 both proximally and distally, thereby closing the distal one-way valve 54b and leaving open only the proximal valve 54a. This forces the blood 56 into the next proximal segment of the vein.

As seen in FIG. 4, as the stimulation ends, the muscles 57 relax (see arrows 58b) which enlarges the vein 50, creating a negative hydraulic pressure which causes the proximal valve 54a to close and the distal valve 54b to open, drawing blood 56 from the next distal segment of the vein.

Figure 5:
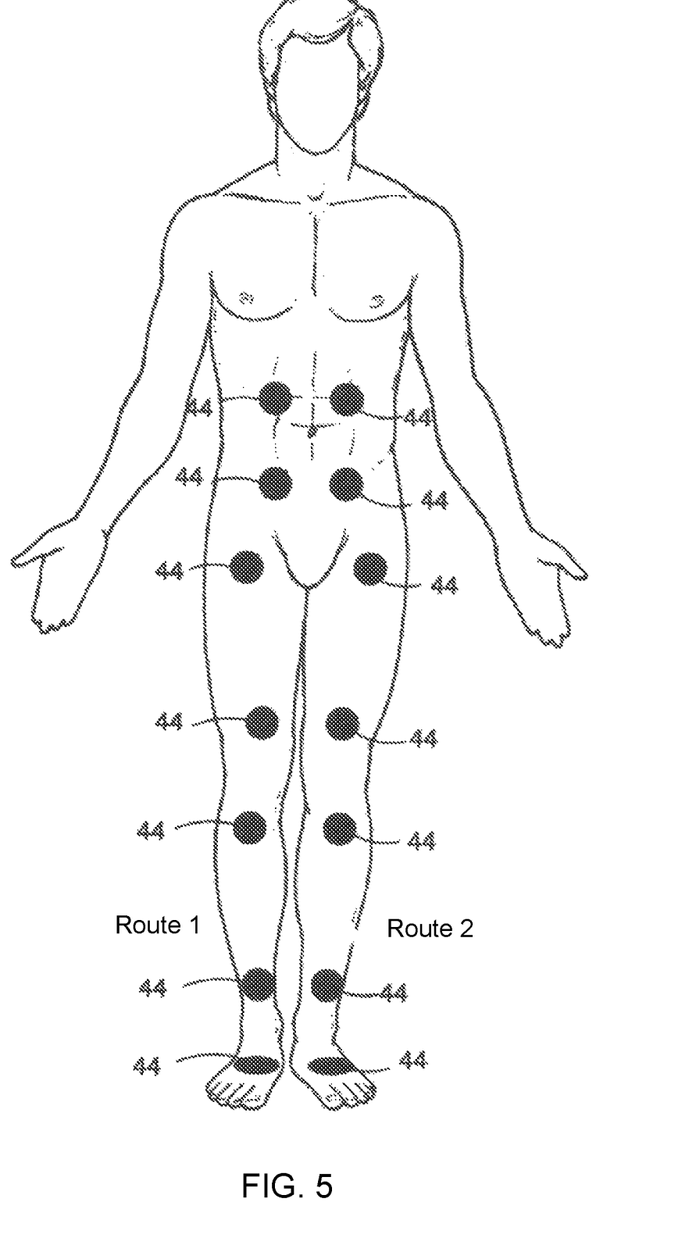
FIG. 5 is a front view of a human body illustrating exemplary placement of treatment pads used with the electrical stimulation system of FIG. 1.

Referring now also to FIG. 5 in the drawings, a front view of a human body illustrating exemplary placement of treating pads 44 as used with system 101 is illustrated. Each pad 44 is in electrical communication with controller 40. The pads 44 are routed so as to follow a continuous vein path back to the heart. A first route is seen in the right leg of the body and a second route is seen in the left leg of the human body. Each route is regulated through controller 40. Each route may be regulated simultaneously or independently. Additionally, the stimulation of the skeletal muscles within each route may be stimulated either simultaneously or independently between the routes. The pads 44 are arranged in pairs wherein each treatment pair is aligned in approximately 180 degree opposed placement relative to one another.

Figure 6:
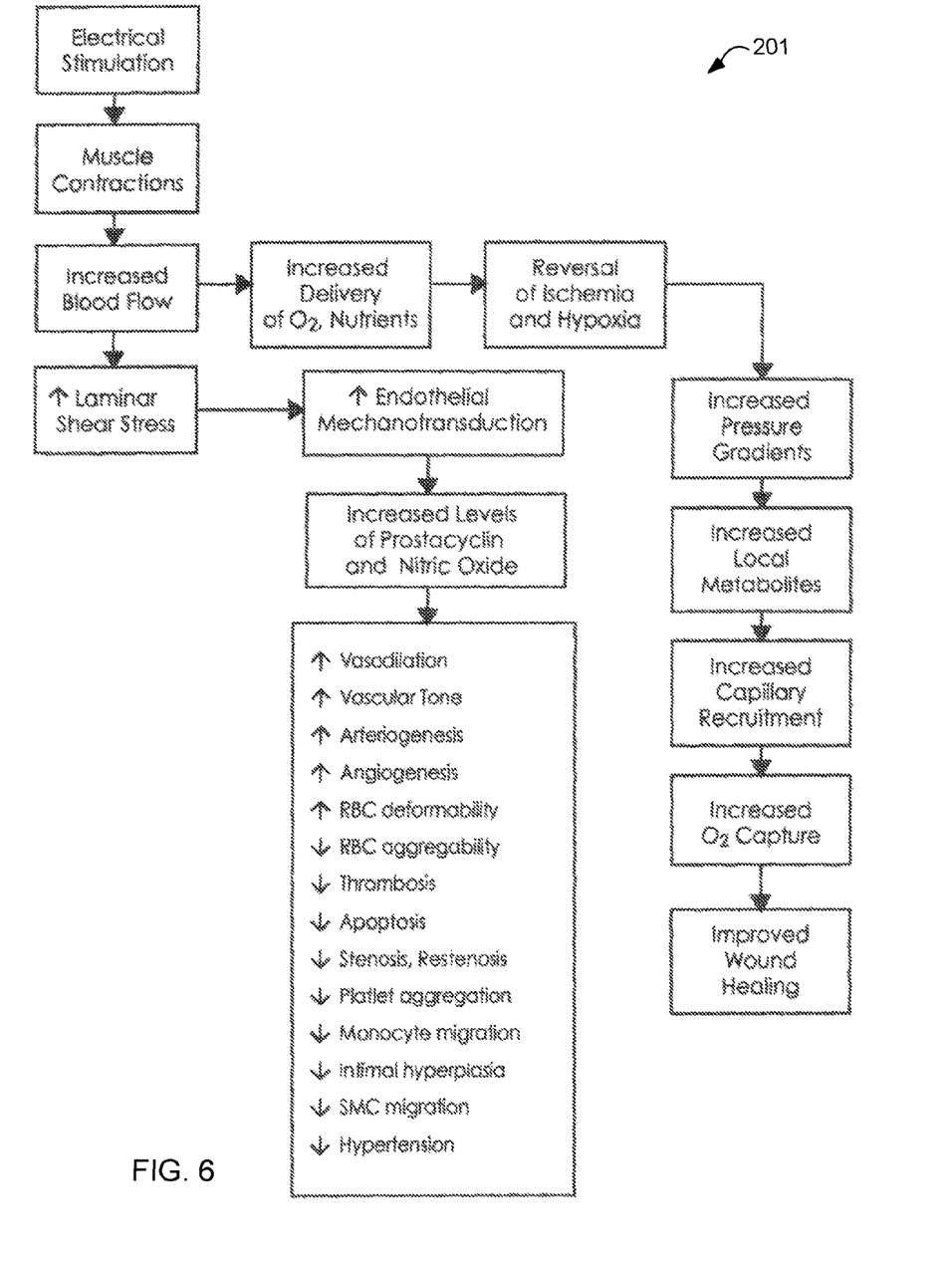
FIG. 6 is flowchart of the method of using the electrical stimulation system of FIG. 1 with its therapeutic effects.

Referring now also to FIG. 6 in the drawings, a flowchart of the method of using system 101 with its therapeutic effects is illustrated. Chart 201 shows the sequence of actions which occur during use of system 101 and the possible therapeutic consequences which result from the application of the present invention to a human subject. As seen in chart 201, controller 40 selectively provides electrical stimulation to leads 42 through pads 44 which thereby contracts the skeletal muscles. This contraction increases the blood flow in the veins which thereby does at least 2 things: (1) increases laminar stresses to induce endothelial mechanotransduction; and (2) increases the delivery of $O_2$ and other nutrients to the body by way of the capillaries. The benefits of each is therein illustrated in chart 201.

This is a unique application method for neuromuscular electrical stimulation requiring the chronic (at least 30-days duration) application of treatments over a large area of the body (all four extremities is the preferred embodiment), and by the overlapping, sequential method in order to create endothelial mechanotransduction at a sufficient magnitude to reach therapeutic levels of vasoactive substances.

The nature and magnitude of shear stress and mechanotransduction play an important role in long-term maintenance of the structure and function of the blood vessel and is an important modulator of cellular function in the cardiovascular system. Data suggests that laminar shear stress stimulates cellular responses that are essential for endothelial cell function and are atheroprotective. Shear stress has an effect on endothelial-mediated alterations in coagulation, leukocyte and monocyte migration, smooth muscle growth, lipoprotein uptake and metabolism, and endothelial cell survival. Endothelial cell response to shear stress includes mechanotransducers (integrins, caveolae, ion channels, and G proteins), intermediate signaling molecules (c-Src, ras, Raf, protein kinase C), the mitogen activated protein kinases (ERK1/2, JNK, p38, BMK-1), and the production of nitric oxide (NO), prostacyclin, aldose reductase and many other vasoactive substances.

As a result of their unique location, endothelial cells experience three primary mechanical forces: (1) pressure, created by the hydrostatic forces of blood within the blood vessel; (2) circumferential stretch or tension, created as a result of defined intercellular connections between the endothelial cells that exert longitudinal forces on the cell; and (3) shear stress, the dragging frictional force created by blood flow. Of these forces, shear stress is a particularly important hemodynamic force because it stimulates mechanotransduction and the release of NO and other vasoactive substances, changes gene expression, cell metabolism, and cell morphology.

NO is a versatile and powerful molecule. It plays a fundamental role in controlling a range of simple bodily functions such as circulation of the blood, activities of the brain, lungs, liver, stomach, kidneys, genitals and other organs. It works in relaxing vascular and non-vascular smooth muscle cells, increasing local blood flow, decreasing local inflammation, inhibiting platelet aggregation and smooth muscle cell proliferation, reducing expression of cell surface adhesion proteins, and controlling neurotransmission. The lack of shear stress leads to a lack of bioavailability of NO, a condition commonly called endothelial dysfunction, and this may provide a mechanism by which risk factors such as hypertension, diabetes, hypercholesterolemia, and sedentary lifestyle act to promote atherosclerosis. Endothelial dysfunction is recognized as a significant health risk which contributes to atherosclerosis, hypertension, heart failure, vasculitis and diabetes.

Use of system 101 results in responses that range from instantaneous ion fluxes and biochemical pathways to gene and protein expression. Through the process of endothelial mechanotransduction, elevated levels of several substances, including nitric oxide, prostacyclin, thrombomodulin, superoxide dismutase, glutathione, Krupple-like factor 2, endothelial progenitor cells, and many others are created or elevated. This combination of increased blood flow (bringing nutrients and oxygen to the tissue) and the therapeutic effects of shear stress, mechanotransduction and the vasoactive substances have wide application and the potential to improve many serious ailments.

Treatment will be given to both lower and upper extremities to have whole-body benefits. Treatment begins by placing treatment pads on the patient in such a manner as to treat in sequential order beginning at the most distal portion with succeeding treatment pads placed proximally on the body. While there are generalized placement parameters, exact placement depends upon the condition being treated and the physiology of the patient. Pads 44 may be placed in anterior-posterior opposition or bilaterally, or other angles which may prove effective.

Once the pads 44 are in place, the operator initiates transmittal of waveforms through the pads 44 to the tissue. Beginning with the most distal pair of treatment pads on one extremity then moving to the next proximal pair of treatment pads, then the next, continuing in like manner until all pads on that extremity are gradually adjusted upward in intensity and the patient's comfort level is broached, then the intensity is slightly reduced. Each successive set of treatment pads is adjusted in like manner until all treatment pads are receiving waveforms just below the outer limits of the patient's comfort zone. After one side of the body has all treatment pads adjusted, proceed to the contralateral extremity and repeat the same sequence of adjustments. Once all treatment pads are receiving waveforms, it may be necessary to adjust the intensity of some or all of the treatment pads.

During the course of treatment, it will be necessary to adjust the intensity up or down (titration) as the patient becomes adjusted to the treatment, or as the nerves become more sensitive to stimulation. The preferred level of treatment is just below the patient's maximum tolerance level.

The treatment will normally last about one hour, but there may be situations where more or less time will be indicated. An example of a possible treatment regimen is to have 3 to 5 treatments a week for 4 to 8 weeks. It is essential that the overall treatment be administered chronically to achieve the full therapeutic benefits. One such desired benefit is the development of collateral circulation which will continue to contribute to blood flow after completion of the course of treatments.

Figure 7:
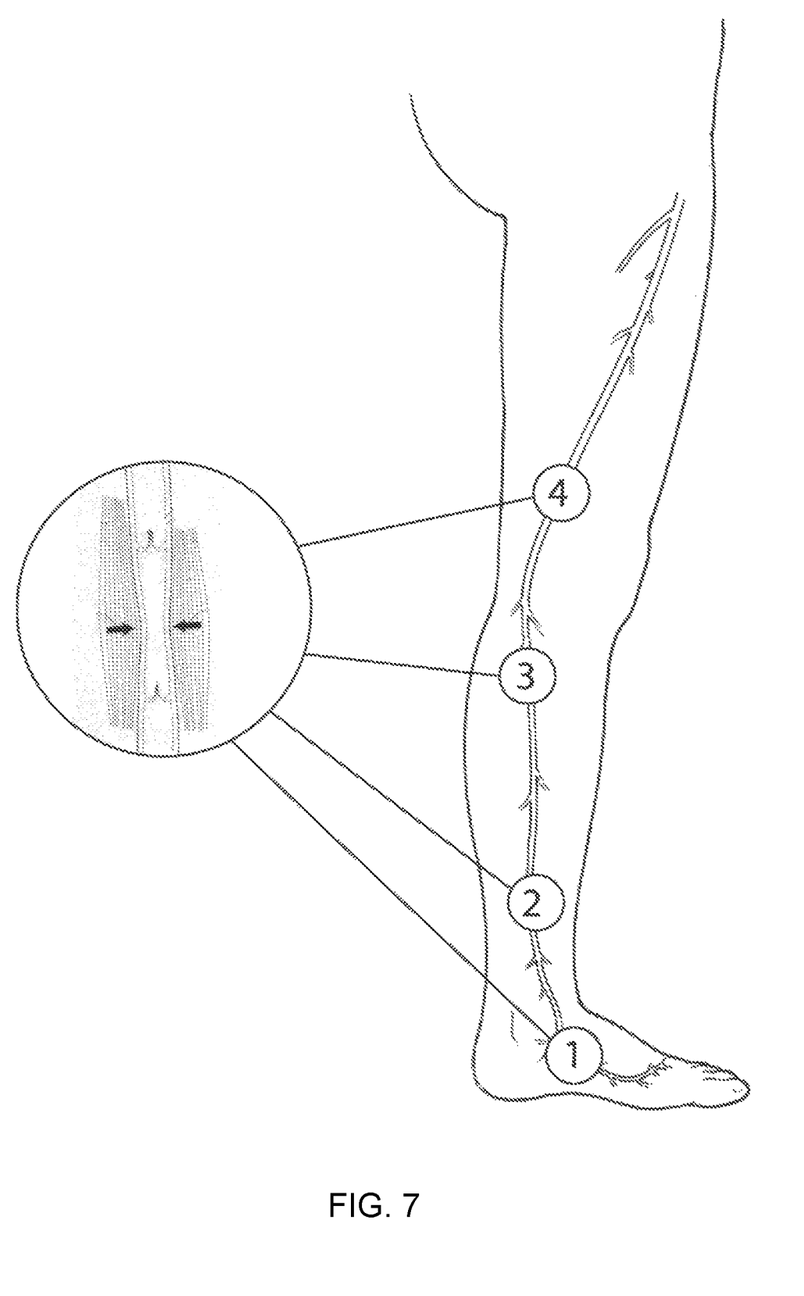
FIG. 7 is an exemplary side view of a human leg showing the pads of FIG. 4 aligned with a particular vein.

Referring now also to FIG. 7 in the drawings, a more detailed exemplary side view of a human leg showing the pads 44 (denoted by the circled numbers 1, 2, 3, and 4) aligned with a particular vein. As seen, the muscles are selectively contracted and released at each location on the extremity.

Figure 8:
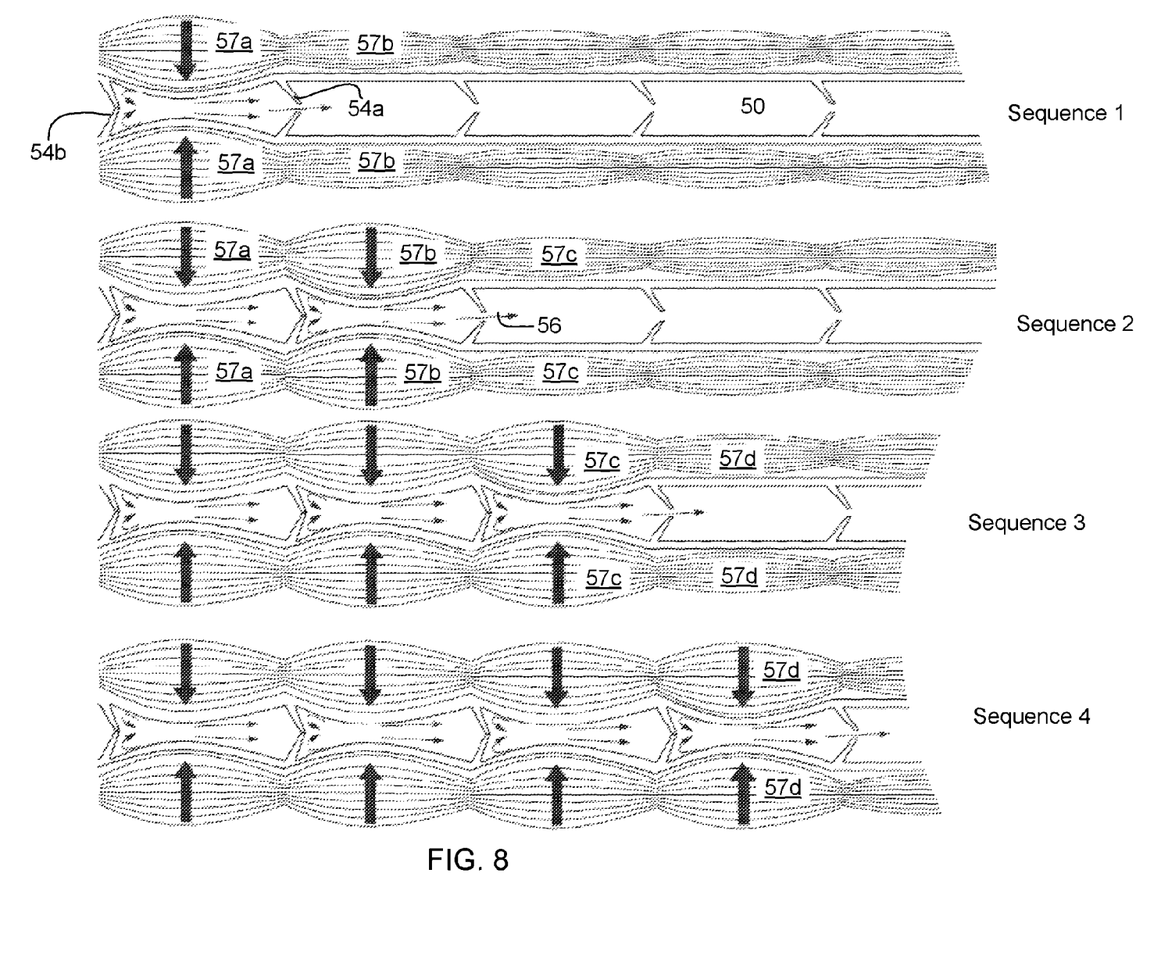
FIG. 8 is an exemplary view showing the sequential operation of the electrical stimulation system of FIG. 1 as used with the treatment pads of FIG. 6.

Referring now also to FIG. 8 in the drawings, the sequential nature of system 101 is shown in more clarity. FIG. 8 shows a single vein having a plurality of muscles 57a/57b with a plurality of valves 54a/54b. The vein is illustrated in four sequences. Each sequence is used to show the operation of controller 40 to induce proper blood flow. In sequence 1, muscle 57a is contracted through electrical stimulation via one or more leads at a particular location on the body. The contraction of those muscles pushes blood out both proximally and distally, thereby closing the distal one-way valve 54b and leaving open only the proximal valve 54a (see also FIGS. 3 and 4). This forces the blood 56 into the next proximal segment of the vein. The valves in all the proximal segments are open to permit blood flow.

While muscles 57a remain contracted, muscles 57b are then also contracted as seen in sequence 2. By maintaining the contraction of muscles 57a while next stimulating the contraction of muscles 57b, the blood is ensured to continue flowing to the next proximal segment. The process continues through the remaining sequential steps (sequence 3 and 4) until all leads in on the vein have been stimulated. The process of maintaining at least two neighboring stimulated muscles at a single time is important. As seen in FIG. 8, system 101 may be configured to sequentially stimulate all muscles in order without the release of any prior muscles until the entire vein has been stimulated. For example, system 101 could be configured to maintain the stimulation of the muscles in sequential order from muscles 57a through each set of muscles until the final set are stimulated (illustrated in sequence 4). It is understood that system 101 may also be configured to selectively cease stimulation of particular muscle groups during the entire sequence. For example, once muscles 57c are stimulated, controller 40 destimulates muscles 57a. With either of the stimulation methods above, once the last muscle group is stimulated, the entire sequence is started over. This repeats itself for a predetermined time frame for each treatment session.

The current application has many advantages over the prior art including at least the following: (1) improves endothelial dysfunction through activation of the endocrine, paracrine and autocrine processes in the endothelium; (2) treating large areas of the body with multiple treatment pads using sequential overlapping intervals of contractions from distal to proximal so as to elevate blood flow and venous return; (3) increase laminar shear stress to trigger endothelial mechanotransduction; and (4) providing the benefits of endogeneous NO (and many other helpful vasoactive substances) and the restoration of endothelial function without the disadvantages and potential side effects of drug use.

The particular embodiments disclosed above are illustrative only, as the application may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. It is apparent that an application with significant advantages has been described and illustrated. Although the present application is shown in a limited number of forms, it is not limited to just these forms, but is amenable to various changes and modifications without departing from the spirit thereof.

What is claimed is:

1. A method for treating vascular dysfunction through neuromuscular stimulation and flow-mediated endothelial mechanotransduction, comprising the steps of:
   providing a controller for the generation of electrical waveforms;
   operably associating the controller to a plurality of treatment pads and a plurality of leads, the leads in electrical communication with the controller;
   coupling the plurality of treatment pads and treatment leads to both the upper and lower extremities of a human body; and
   initiating an electrical stimulation signal through the leads and into the tissue of the body, the controller regulating the electrical stimulation signal;
   wherein the electrical stimulation signal is configured to contract skeletal muscle on the body to induce endothelium mechanotransduction in a blood vessel, the endothelium mechanotransduction resulting from induced frictional drag between blood cells and an endothelial layer of the blood vessel, the endothelium mechanotransduction activating both paracrine and autocrine process; and
   wherein the electrical stimulation signal is regulated through the plurality of treatment pads and leads in a sequential manner with overlapping intervals of contractions from a distal end to a proximal end of each extremity.

2. The method of claim 1, wherein the waveforms are provided in a plurality of sequential treatment intervals from distal to proximal on each extremity.

3. The method of claim 2, wherein the treatment intervals vary in length between one half second to a plurality of seconds.

4. The method of claim 2, wherein each treatment interval commences before a preceding treatment interval ends, providing overlap of said treatment intervals.

5. The method of claim 1, wherein the plurality of pads are distributed along a route of at least one extremity of the human body.

6. The method of claim 5, wherein the plurality of pads are aligned in pairs and located in an opposed placement to one another.

7. The method of claim 1, wherein the controller is configured to regulate at least one of the duration, intensity, sequence, and form of the waveform.

8. The method of claim 1, wherein communication between the controller and the plurality of leads is performed through one or more wires.

9. The method of claim 1, wherein communication between the controller and the plurality of leads is performed through wireless signals.

10. The method of claim 1, wherein the pads are coupled to the dermal surface of the body by at least one of the following methods including an adhesive, a strap, a hook and loop fastener, an elastic member, and a garment.

11. The method of claim 1, further comprising:
   adjusting intensities throughout each treatment and the entire series of treatments in response to changing conditions of the tissue being treated.

12. The method of claim 1, further comprising:
   adjusting the waveform during the treatment for sufficient intensity to contract skeletal muscles and activate the venous muscle pump.

13. The method of claim 1, wherein the electrical stimulation signal is of sufficient intensity and sequentially provided, will activate a venous muscle pump and create elevated levels of blood flow delivering elevated levels of nutrients and oxygen to the skeletal muscle.

14. The method of claim 1, wherein the electrical stimulation signal is configured to selectively contract the skeletal muscle so as to elevate blood flow in the blood vessels, the elevated blood flow will increase laminar shear stresses on the endothelium of the blood vessel and thus induce or elevate endothelial mechanotransduction resulting in increased production of vasoactive substances including, but not limited to nitric oxide, prostacyclin, thrombomodulin, glutathione, Krupple-like factor 2, endothelial progenitor cells, C peptides, carbon monoxide, bradykinin, superoxide dismutase, adenosine, thioredoxin, adrenomedullin, heme oxygenase-1, and granulocyte-macrophage colony stimulating factor.

15. The method of claim 1, further comprising:
elevating the intensity of the electrical stimulation on the body to bring some discomfort.

16. The method of claim 1, wherein the waveform includes large inter-pulse spacing without ramping.

17. The method of claim 1, further comprising:
adjusting the electrical stimulation signal for each extremity individually and in sequential order.

18. The method of claim 1, further comprising:
adjusting the intensity of the electrical stimulation signal in response to nerve sensitivity during treatment.

* * * * *